United States Patent
Ratti

(10) Patent No.: US 6,210,968 B1
(45) Date of Patent: *Apr. 3, 2001

(54) **DNA MOLECULES ENCODING PGP3 PROTEIN FROM *CHLAMYDIA TRACHOMATIS***

(75) Inventor: Giulio Ratti, Siena (IT)

(73) Assignee: Chiron SpA (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/465,465

(22) Filed: Jun. 5, 1995

Related U.S. Application Data

(62) Division of application No. 08/229,980, filed on Apr. 19, 1994.

(51) Int. Cl.$^7$ .............................. C12N 15/00; C12N 1/20; C12P 21/06; C07H 21/04
(52) U.S. Cl. ...................... 435/476; 435/69.1; 435/488; 435/252.3; 435/252.33; 435/320.1; 530/300; 530/350; 536/23.7
(58) Field of Search ................ 435/69.1, 172.1, 435/252.33, 320.1, 476, 488, 252.3; 530/300, 350; 536/23.7

(56) References Cited

U.S. PATENT DOCUMENTS

| | | | |
|---|---|---|---|
| 4,336,336 | 6/1982 | Silhavy et al. | 435/172 |
| 4,546,083 | 10/1985 | Meyers et al. | 435/240 |
| 4,551,433 | 11/1985 | DeBoer | 435/253 |
| 4,588,684 | 5/1986 | Brake | 435/68 |
| 4,683,195 | 7/1987 | Mullis et al. | 435/6 |
| 4,683,202 | 7/1987 | Mullis | 435/91 |
| 4,689,406 | 8/1987 | Banks et al. | 536/27 |
| 4,738,921 | 4/1988 | Belagaje et al. | 435/68 |
| 4,745,056 | 5/1988 | Guterman et al. | 435/68 |
| 4,837,148 | 6/1989 | Cregg | 435/172.3 |
| 4,870,008 | 9/1989 | Brake | 435/70 |
| 4,876,197 | 10/1989 | Burke et al. | 435/172.3 |
| 4,880,734 | 11/1989 | Burke et al. | 435/68 |
| 4,929,555 | 5/1990 | Cregg et al. | 435/172.3 |

FOREIGN PATENT DOCUMENTS

| | | |
|---|---|---|
| 036259 | 9/1981 | (EP) . |
| 036776 | 9/1981 | (EP) . |
| 060057 | 9/1982 | (EP) . |
| 121775 | 10/1984 | (EP) . |
| 127839 | 12/1984 | (EP) . |
| 136829 | 4/1985 | (EP) . |
| 136907 | 4/1985 | (EP) . |
| 155476 | 9/1985 | (EP) . |
| 164556 | 12/1985 | (EP) . |
| 196056 | 10/1986 | (EP) . |
| 219237 | 4/1987 | (EP) . |
| 293079 * | 4/1987 | (EP) . |
| 244042 | 11/1987 | (EP) . |
| 267851 | 5/1988 | (EP) . |
| 284044 * | 9/1988 | (EP) . |
| WO 90/14837 * | 5/1989 | (EP) . |
| 324274 * | 7/1989 | (EP) . |
| 324647 * | 7/1989 | (EP) . |
| 329203 * | 8/1989 | (EP) . |
| 449681 * | 8/1992 | (EP) . |
| 62-96086 * | 5/1987 | (JP) . |

OTHER PUBLICATIONS

Comanducci, M. et al., "Diversity of the *Chlamydia trachomatis* Common Plasmid in Biovars with Different Pathogenicity", *Plasmid* 1990, 23, 149–154.

Comanducci, M. et al., "Expression of a Plasmid Gene of *Chlamydia trachomatis* Encoding a Novel 28 kDa Antigen", *J. of Gen. Microbiology* 1993, 139, 1083–1092.

Tabor, S. and Richardson, "A Bacteriophage T7 RNA Polymerase/Promoter System for Controlled Exclusive Expression of Specific Genes", *PNAS USA* 1985, 82, 1074–1078.

Birkelund, S., The Molecular Biology and Diagnostics of *Chlamydia trachomatis*, *Dan. Med. Bull.* Aug. 1992, 39(4), 304–320.

Harlowe et al., Antibodies: A Laboratory Manual, Cold Spring Harbor Laboratory, Cold Spring, New York, pp. 33–34, 564, 1988.

Clark et al., "Enzyme linked Immunsorbent Assay (FUSA): Theoretical and Practical Aspects", in "Enzyme–Immunoassay", CRC Press, Inc., pp. 167–179, 1987.

Comanducci, M. et al., "Identification and Characterization of a 28–Kd Protein of *C.trachomatis* Encoded by the 7.5–Kb Common Plasmid", International Symposium of Human Chlamydial infections, Jun. 24–29, 1990, pp. 121–124.

Morrison et al., "Immunology of *Chlamydia trachomatis* Infections Immunoprotective and Immunopathogenetic Responses", in "Sexually Transmitted Diseases", Quinn, T. Ed., Raven Press, Ltd, New York, pp. 57–84, 1992.

Zhang, Y.–X. et al., "Protective Monoclonal Antibodies to *Chlamydia trachomatis* Serovar– and Serogroup–Specific Major Outer Membrane Protein Determinants", *Infection and Immunity* 1989, 57(2), 636–638.

Allen, G. et al., "Synthesis and Cloning of a Gene Coding for a Fusion Protein Containing Mouse Epidermal Growth Factor", *J. of Biotechnology* 1987, 5, 93–114.

Amann, E. et al., "Vectors Bearing a Hybrid trp–lac Promoter Useful for Regulated Expression of Cloned Genes in *Escherichia coli*", *Gene* 1983, 25, 167–178.

(List continued on next page.)

*Primary Examiner*—Lisa J. Hobbs
(74) *Attorney, Agent, or Firm*—Robert P. Blackburn; Alisa A. Harbin; Woodcock Washburn Kurtz Mackiewicz & Norris LLP

(57) ABSTRACT

A new recombinant form of the plasmid-encoded protein pgp3 from *C. trachomatis*, serotype D, was purified by ion exchange column chromatography and shown to be suitable for quantitative immunoassy on clinical samples in an ELISA format.

4 Claims, 1 Drawing Sheet

OTHER PUBLICATIONS

Amann, E. And Brosius, "'ATG Vectors' for Regulated High–Level Expression of Cloned Genes in *Escherichia coli*", *Gene* 1985, 40, 183–190.

Augustin, J. and Götz, "Transformation of *Staphylococcus epidermidis* and Other Staphylococcal Species with Plasmid DNA by Electroporation", *FEMS Microbiology Letters* 1990, 66, 203–208.

Ausubel, ed., "Current Protocols in Molecular Biology", vol. 2, John Wiley & Sons, 1994, Section 16.8.

Barany, F. And Tomasz, "Genetic Transformation of *Streptococcus pneumoniae* by Heterologous Plasmid Deoxyribonucleic Acid", *J. of Bacteriology* 1980, 144, 698–709.

Beach, D. et al., "Functionally Homologous Cell Cycle Control Genes in Budding and Fission Yeast", *Nature* Dec. 30, 1982, 300, 706–709.

Birnstiel, M.L. et al., "Transcription Termination and 3' Processing: The End Is In Site!", *Cell* 1985, 41, 349–359.

Boshart, M. et al., "A Very Strong Enhancer is Located Upstream of an Immediate Early Gene of Human Cytomegalovirus", *Cell* 1985, 41, 521–530.

Botstein, D. et al., "Sterile Host Yeasts (SHY): A Eukaryotic System of Biological Containment for Recombinant DNA Experiments", *Gene* 1979, 8, 17–24.

Brake, A. et al., "α–Factor–Directed Synthesis and Secretion of Mature Foreign Proteins in *Saccharomyces cerevisiae*", *PNAS USA* 1984, 81, 4642–4646.

Butt, T. And Ecker, "Yeast Metallothionein and Applications in Biotechnology", *Microbiological Reviews* Sep. 1987, 51(3), 351–364.

Carbonell, L. et al., "Baculovirus–Mediated Expression of Bacterial Genes in Dipteran and Mammalian Cells", *J. of Virology* Oct. 1985, 56(1), 153–160.

Carbonell, L. et al., "Synthesis of Gene Coding for an Insect–Specific Scorpion Neutrotoxin and Attempts to Express It Using Baculovirus Vectors", *Gene* 1988, 73, 409–418.

Cerrone, M. et al., "Cloning and Sequence of the Gene for Heat Shock Protein 60 from *Chlamydia trachomatis* and Immunological Reactivity of the Protein", *Infection and Immunity* Jan. 1991, 59(1), 79–90.

Chassy, B. and Flickinger, "Transformation of *Lactobacillus casei* by Electroporation", *FEMS Microbiology Letters* 1987, 44, 173–177.

Cohen, J. et al., "Functional Expression in Yeast of the *Escherichia coli* Plasmis Gene Coding for Chloramphenicol Acetyltransferase", *PNAS USA* Feb. 1980, 77(2), 1078–1082.

Cohen, S. et al., "Nonchromosomal Antibiotic Resistance in Bacteria: Genetic Transformation of *Escherichia coli* by R–Factor DNA", *PNAS USA* Aug. 1972, 69(8), 2110–2114.

Cregg, J. et al., "*Pichia pastoris* as a Host System for Transformations", *Mol. and Cellular Biology* Dec. 1985, 5(12), 3376–3385.

Das, S. et al., "Transformation of *Kluyveromyces fragilis*", *J. of Bacteriology* Jun. 1984, 158(3), 1165–1167.

Davidow, L. et al., "Integrative Transformation of the Yeast *Yarrowia lipolytica*", *Curr. Genet.* 1985, 10, 39–48.

Davies, J. and Smith, "Plasmid–Determined Resistance to Antimicrobial Agents", *Ann. Rev. Microbiol* . . . 1978, 32, 469–518.

De Boer, H. et al., "The TAC Promoter: A Functional Hybrid Derived from the trp and lac Promoters", *PNAS USA* Jan. 1983, 80, 21–25.

De Louvencourt, L. et al., "Transformation of *Kluyveromyces lactis* by Killer Plasmid DNA", *J. of Bacteriology* May 1983, 154(2), 737–742.

Dijkema, R. et al., "Cloning and Expression of the Chromosomal Immune Interferon Gene of the Rat", *The EMBO Journal* 1985, 4(3), 761–767.

Dower, W. et al., "High Efficiency Transformation of *E. Coli* by High Voltage Electroporation", *Nucleic Acids Res.* 1988, 16(13), 6127–6145.

Fiedler, S. and Wirth, "Transformation of Bacteria with Plasmid DNA by Electroporation", *Analytical Biochem.* 1988, 170, 38–44.

Fraser, M.J., "Expression of Eucaryotic Genes in Insect Cell Cultures", *In Vitro Cellular & Developmental Biology* Mar. 1989, 25(3) Part I, 225–235.

Friesen, P.D. and Miller, "The Regulation of Baculovirus Gene Expression", *Current Topics in Microbiology* 1986, 131, 31–49.

Gaillardin, C. et al., "Integrative Transformation of the Yeast *Yarrowia lipolytica*", *Curr. Genet.* 1985, 10, 49–58.

Ghrayeb, J. et al., "Secretion Cloning Vectors in *Escherichia coli*", *The EMBO J.* 1984, 3(10), 2437–2442.

Gleeson, M.A. et al., "Transformation of the Methylotrophic Yeast *Hansenula polymorpha*", *J. of Gen. Microbiol* . . . 1986, 132, 3459–3465.

Gluzman, Y., "SV40–Transformed Simian Cells Support the Replication of Early SV40 Mutants", *Cell* Jan. 1981, 23, 175–182.

Goeddel, D. et al., "Synthesis of Human Fibroblast Interferon by *E. coli*", *Nucleic Acids Res.* 1980, 8(18), 4057–4074.

Gorman, C. et al., "The Rous Sarcoma Virus Long Terminal Repeat is a Strong Promoter When Introduced Into a Variety of Eukaryotic Cells By DNA–Mediated Transfection", *PNAS USA* Nov. 1982, 79, 6777–6781.

Green, M.R., "Pre–mRNA Splicing", *Ann. Rev. Genet.* 1986, 20, 671–708.

Harlander, S., "Transformation of *Streptococcus lactis* by Electroporation", in "Streptococcal Genetics", Ferretti and Curtiss III, eds., Am. Soc. For Microbiology, Washington, D.C. 1987.

Hatt, C. et al., "Analysis of the Entire Nucleotide Sequence of the Cryptic Plasmid of *Chlamydia trachomatis* Serovar L1. Evidence for Invovlement in DNA Replication", *Nucleic Acids Res.* 1988, 16(9), 4053–4067.

Henikoff, S. et al., "Isolation of a Gene from Drosophila By Complementation in Yeast", *Nature* 1981, 289, 33–37.

Hinnen, A. et al., "Transformation of Yeast", *PNAS USA* Apr. 1978, 75(4), 1929–1933.

Hollenberg, C., "The Expression of Bacterial Antibiotic Resistance Genes in the Yeast *Saccharomyces cerevisiae*", in "Plasmids of Medical, Environmental and Commercial Importance", Timmis and Pühler, eds., Elsevier/North–Holland Biomedical Press, 1979, pp. 481–492.

Hollenberg, C.P., "Cloning with 20–μm DNA Vectors and the Expression of Foreign Genes in *Saccharomyces cerevisiae*", *Current Topics Microbiol . . . Immunol.* 1981, 96, 119–144.

Inouye, M., "Experimental Manipulation of Gene Expression", Academic Press, New York, 1983.

Ito, H. et al., "Transformation of Intact Yeast Cells Treated with Alkali Cations", *J. of Bacteriol.* 1983, 153(1), 163–168.

Jia, S. et al., "Carbohydrate–Binding Protein 35: Molecular Cloning and Expression of a Recombinant Polypeptide with Lectin Activity in *Escherichia coli*", *Gene* 1987, 60, 197–204.

Ju, Y.S. et al., "Effect of Naloxon on Counter Insulin Hormone Secretion in Insulin–Induced Hypoglycemia", *The Korean J. of Internal medicine* Jul., 1987, 2(2), 190–195.

Kaufman, R. et al., "The Phosphorylation State of Eucaryotic Initiation Factor 2 Alters Translational Efficiency of Specific mRNAs", *Mol. and Cellular Biol.* Mar. 1989, 9(3), 946–958.

Krainer, A. and Maniatis, "RNA Splicing", in "Transcription and Splicing", Hames and Glover, eds., IRL Press, pp. 131–207.

Kunze, G. et al., "Transformation of the Industrially Important Yeasts *Candida maltosa* and Pichia guilliermondii", *J. Basic Microbiol* . . . 1985, 25(2), 141–144.

Kurtz, M. et al., "Integrative Transformation of *Candida albicans*, Using a Cloned Candida ADE2 Gene", *Mol. and Cell. Biol.* Jan. 1986, 6(1), 142–149.

Kushner, S., "Improved Method for Transformation of *Escherichia coli* With ColE1 Derived Plasmids", in "Genetic Engineering", Proceedings of the Int. Symposium on Genetic Engineering, Milan, Italy, Mar. 29–31, 1978. Published by Elsevier/North–Holland Press, Amsterdam, 1978, pp. 17–23.

Lebacq–Verheyden, A.–M. et al., "Posttranslational Processing of Endogenous and of Baculovirus–Expressed Human Gastrin–Releasing Peptide Precursor", *Mol. and Cell. Biol.* Aug. 1988, 8(8), 3129–3135.

Luckow, V. and Summers, "High Level Expression of Nonfused Foreign Genes with *Autographa californica* Nuclear Polyhedrosis Virus Expression Vectors", *Virology* 1989, 170, 31–39.

Maeda, S. et al., "Production of Human α–Interferon in Silkworm Using a Baculovirus Vector", *Nature* Jun. 13, 1985, 315, 592–594.

Makoff, A. et al., "Translational Fusions with Fragments of the trpE Gene Improve the Expression of a Poorly Expressed Heterologous Gene in *Escherichia coli*", *J. of Gen. Microbiol* . . . 1989, 135, 11–24.

Mandel, M. and Higa, "Calcium–Dependent Bacteriophage DNA Infection", *J. Mol. Biol.* 1970, 53, 159–162.

Maniatis, T. et al., "Regulation of Inducible and Tissue–Specific Gene Expression", *Science* Jun. 5, 1987, 236, 1237–1245.

Martin, B. et al., "Glycosylation and Processing of High Levels of Active Human Glucocerebrosidase in Invertebrate Cells Using a Baculovirus Expression Vector", *DNA* 1988, 7(2), 99–106.

Masson, L. et al., "Transformation of *Bacillus thuringiensis* Vegetative Cells by Electroporation", *FEMS Microbiology Letters* 1989, 60, 273–278.

Mercereau–Puijalon, O. et al., "Synthesis of a Chicken Ovalbumin–Like Protein in the Yeast *Saccharomyces cerevisiae*", *Gene* 1980, 11, 163–167.

Miller, H. et al., "Cloning and Expression of a Yeast Ubiquitin–Protein Cleaving Activity in *Escherichia coli*", *Bio/Technology* 1989, 7, 698–704.

Miller, L., "Insect Baculoviruses: Powerful Gene Expression Vectors", *BioEssays* 1989, 11(4), 91–95.

Miller, J. et al., "High–Voltage Electroporation of Bacteria: Genetic Transformation of *Campylobacter jejuni* With Plasmid DNA", *PNAS USA* 1988, 85, 856–860.

Miller, L., "Baculoviruses as Gene Expression Vectors", *Ann. Rev. Microbiol* . . . 1988, 42, 177–199.

Miyajima, A. et al., "Use of the Silkworm, *Bombyx mori*, and an Insect Baculovirus Vector for High–Level Expression and Secretion of Biologically Active Mouse Interleukin–3", *Gene* 1987, 58, 273–281.

Miyanohara, A. et al., "Expression of Hepatitis B Surface Antigen Gene in Yeast", *PNAS USA* 1983, 80, 1–5.

Nagai, K. and Thogersen, "Generation of β–Globin by Sequence–Specific Proteolysis of a Hybrid Protein produced in *Escherichia coli*", *Nature* 1984, 309, 810–812.

Nevins, J., "The Pathway of Eukaryotic mRNA Formation", *Ann. Rev. Biochem.* 1983, 52, 441–466.

Oka, T. et al., "Synthesis and Secretion of Human Epidermal Growth Factor by *Escherichia coli*", *PNAS USA* 1985, 82, 7212–7216.

Orr–Weaver, T. et al., "Genetic Applications of Yeast Transformation with Linear and Gapped Plasmids", *Methods in Enzymology* 1983, 101, 228–245.

Padgett, R. et al., "Splicing of Messenger RNA Precursors", *Ann. Rev. Biochem.* 1986, 55, 1119–1150.

Palva, I. et al., "Secretion of *Escherichia coli* β–Lactamase from *Bacillus subtilis* by the Aid of a α–Amylase Signal Sequence", *PNAS USA* 1982, 79, 5582–5586.

Panthier, J.–J. et al., "Cloned β–Galactosidase Gene of *Escherichia coli* is Expresed in the Yeast *Saccharomyces cerevisiae*", *Current Genetics* 1980, 2, 109–113.

Perry, D. and Kuramitsu, "Genetic Transformation of *Streptococcus mutans*", *Infection and Immunity* 1981, 22(3), 1295–1297.

Powell, I. et al., "A Simple and Rapid Method for Genetic Transformation of Lactic Streptococci by Electroporation", *Applied and Environmental Microbiology* 1988, 54(3), 655–660.

Proudfoot, N.J. and Whitelaw, "Termination and 3' End Processing of Eukaryotic RNA", in "Transcription and Splicing", Hames, B.D. and Glover, Eds., IRL Press, Oxford, 1988.

Proudfoot, N.J., "How RNA Polymerase II Terminates Transcription in High Eukaryotes", *TIBS* 1989, 14, 105–110.

Raibaud, O. and Schwartz, "Positive Control of Transcription Initiation in Bacteria", *Ann. Rev. Genet.* 1984, 18, 173–206.

Rine, J. et al., "Targeted Selection of Recombinant Clones Through Gene Dosage Effects", *PNAS USA* 1983, 80, 6750–6754.

Roggenkamp, R. et al., "Transformation of the Methylotrophic Yeast *Hansenula polymorpha* by Autonomous Replication and Integration Vectors", *Mol. Gen. Genet.* 1986, 202, 302–308.

Saiki, R. et al., "Analysis of Enzymatically Amplified β–Globin and HLA–DQα DNA with Allele–Specific Oligonucleotide Probes", *Nature* 1986, 324, 163–166.

Sambrook, "Molecular Cloning A Laboratory Manual", Chapter 16, Cold Spring Harbor Press, 1989.

Sambrook, "Molecular Cloning A Laboratory Manual", Chapter 17, Cold Spring Harbor Pres, 1989.

Sassone–Corsi and Borrelli, "Transcriptional Regulation by trans–Acting Factors", *TIBS* Aug. 1986, 215–219.

Scharf, S. et al., "Direct Cloning and Sequence Analysis of Enzymatically Amplified Genomic Sequences", *Science* 1986, 1076–1078.

Shimatake, H. and Rosenberg, "Purified λ Regulatory Protein cII Positively Activates Promoters for Lysogenic Development", *Nature* 1981, 292, 128–132.

Shimizu, Y. et al., "Transfer of Cloned Human Class I Major Histocompatibility Complex Genes Into HLA Mutant Human Lymphoblastoid Cells", *Mol. and Cell. Biology* 1986 6(4), 1074–1087.

Shine, J. and Dalgarno, "Determinant of Cistron Specificity in Bacterial Ribosomes", *Nature* 1975, 254, 34–38.

Smith, G. et al., "Production of Human Beta Interferon in Insect Cells Infected with a Baculovirus Expression Vector", *Molecular and Cellular Biology* 1983, 3(12), 2156–2165.

Smith, G. et al., "Modification and Secretion of Human Interleukin 2 Produced in Insect Cells by a Baculovirus Expression Vector", *PNAS USA* 1985, 82, 8404–8408.

Sriprakash, K.S. and MacAvoy, "A Gene for dnaB Like Protein in Chlamydial Plasmid", *Nucleic Acids Res.* 1987, 15(24), 10596.

Sriprakash, K.S. and MacAvoy, "Characterization and Sequence of a Plasmid from the Trachoma Biovar and *Chlamydia trachomatis*", *Plasmid* 1987, 18, 205–214.

Somkuti, G.A. and Steinberg, "Genetic Transformation of *Streptococcus thermophilus* by Electroporation", Proc. 4th Eur. Congress on Biotechnology Jun. 14–19, 1987, vol. 1, Neijssel,O.M.et al., eds., Elsevier, Amsterdam, 1987.

Steitz, J.A., "Genetic Signals and Nucleotide Sequences in Messenger RNA", in "Biological Regulation and Development", vol.1, Goldberger, R., ed., Plenum Press, New York, 1979.

Stinchcomb, D. et al., "Centromeric DNA from *Saccharomyces cerevisiae*", *J. Mol. Biol.* 1982, 158, 157–179.

Studier, F. William and Moffatt, "Use of Bacteriophage T7 RNA Polymerase to Direct Selective High–Level Expression of Cloned Genes", *J. Mol. Biol.* 1986, 189, 113–130.

Summers, M. and Smith, "A Manual of Methods for Baculovirus Vectors and Insect Cell Culture Procedures", Texas Agricultural Experiment Station Bulletin No. 1555, May, 1987.

Taketo, A., "DNA Transfection of *Escherichia coli* by Electroporation", *Biochimica et Biophysica Acta* 1988, 949, 318–324.

Van den Berg, J. et al., "Kluyveromyces as a Host for Heterologous Gene Expression: Expression and Secretion of Prochymosin", *Bio/Technology* Feb., 1990, 8, 135–139.

Vlak, J., "Functional Studies on the p10 Gene of *Autographa californica* Nuclear Polyhedrosis Virus Using a Recombinant Expressing a p10–β–Galactosidase Fusion Gene", *J. Gen. Virol.* 1988, 69, 765–776.

Wright, K., "Insect virus as Super–Vector?", *Nature* 1986, 321, 718.

Wang, Y. and Taylor, "Natural Transformation in Campylobacter Species", *J. of Bacteriology* 1990, 172(2), 949–955.

Yelverton, E. et al., "Bacterial Synthesis of a Novel Human Leukocyte Interferon", *Nucleic Acids Res.* 1981, 9(3), 731–741.

Sambrook et al., "Molecular Cloning: a Laboratory Manual", 2nd Edition, 1989.

Glover, D.N., ed., "DNA Cloning", vols. I and II, 1985.

Gait, M.J., ed., "Oligonucleotide Synthesis", 1984.

Hames, B.D. and Higgins, eds., "Nucleic Acid Hybridization", 1984.

Freshney, R.I., ed., "Animal Cell Culture", 1986.

"Immobilized Cells and Enzymes", IRL Press, 1986.

Perbal, V., "A Practical Guide to Molecular Cloning", 1984.

"Methods in Enzymology", particularly vols. 154 and 155, Wu and Grossman and Wu, eds., respectively, Academic Press, Inc. Dec. 1987.

Miller, J.H. and Calos, eds., "Gene Transfer Vectors for Mammalian Cells", 1987, Cold Spring Harbor Laboratory.

Mayer and Walker, eds., "Immunochemical Methods in Cell and Molecular Biology", Academic Press, London, 1987.

Scopes, "Protein Purification: Principles and Practice", Springer Verlag, NY, 1987.

Wier, D.M. and Blackwell, eds., "Handbook of Experimental Immunology", vol. I–IV, 1986.

Comanducci, M., et al., "The Structure of a Plasmid of Chlamydia Trachomatis Believed to be Required for Growth within Mammalian Cells", *Mol. Micro.* 1988, 2(4) 531–538.

Georgiou, G. (1988) Optimizing the Production of Recombinant Proteins in Microorganism. AIChE J. 34(8): 1233–1248.

Kahane, S. et al., "Cloning, characterization and sequece of novel 59–kDa protein of *Chlamydia trachomatis*," Gene, 90:61–67, 1990.

Koehler, J. E. et al., "Overexpression and surface localization of the *Chlamydia trachomatis* major outer membrane protein protein in *Escherichia coli*,"*Molecular Microbiology*, 6(9):1087–1094, 1992.

Comanducci, M. et al., "The Structure of a Plasmid of Chlamydia Trachomatis Belived to be Requried for Growth within Mannalian Cells", *Mol. Micro.* 1988, 2 (4) 531–538.

* cited by examiner

DNA MOLECULES ENCODING PGP3 PROTEIN FROM *CHLAMYDIA TRACHOMATIS*

CROSS-REFERENCE TO RELATED APPLICATIONS

This application is a divisional of application Ser. No. 229,980, filed on Apr. 19, 1994, pending.

FIELD OF THE INVENTION

A new recombinant form of the plasmid-encoded protein pgp3 from *C. trachomatis*, serotype D, was purified by ion exchange column chromatography and shown to be suitable for quantitative immunoassay on clinical samples in an ELISA format. Since initial attempts of developing a similar assay with a SDS-denatured pgp3-fusion protein failed, the results suggest that for anti-pgp3 antibody detection, antigen conformation is important.

BACKGROUND OF THE INVENTION

The function of the 7.5 kb plasmid, pCT, of *Chlamydia trachomatis* is still unknown. However the fact that this DNA element appears to be strongly conserved in *C. trachomatis* (both in terms of its presence in essentially all isolates and in terms of its genetic structure) suggests that pCT may provide some important, and perhaps advantageous, function to the chlamydial cell during its natural host infection. Recently, an open reading frame of pCT (ORF3; Comanducci, et al., *Plasmid,* 1990, 23, 149–154 was expressed in *E. coli* as a recombinant fusion protein Comanducci, et al., *J. Gen. Microbiol.*, 1993, 139, 1083–1092. The expression system used added a 11-kDa N-terminal polypeptide of the MS2-bacteriophage polymerase to the 28-kDa polypeptide (pgp3) encoded by ORF3. The resulting 39-kDa product was used to show that pgp3 epitopes can be recognized on Western blots by antibodies present in sera from patients with chlamydial infections, but not in control sera from healthy donors. Following this observation, we subsequently tried to develop a serological test more suitable than the immunoblotting technique for obtaining reproducible and quantitative data from large numbers of clinical samples. We now report that an enzyme-linked immunoassay based on a new recombinant form of the pgp3 protein, can be used for assessing the prevalence of pgp3 antibodies in people with *C. trachomatis* infections.

SUMMARY OF THE INVENTION

The invention relates to a recombinant polynucleotide encoding a recombinant *Chlamydia trachomatis* pgp3 protein.

The invention also relates to a vector comprising a recombinant polynucleotide encoding a recombinant *Chlamydia trachomatis* pgp3 protein.

The invention also relates to a host cell transformed with a vector comprising a recombinant polynucleotide encoding a recombinant *Chlamydia trachomatis* pgp3 protein.

RECOMBINANT ANTIGEN PREPARATION

Figure 1:
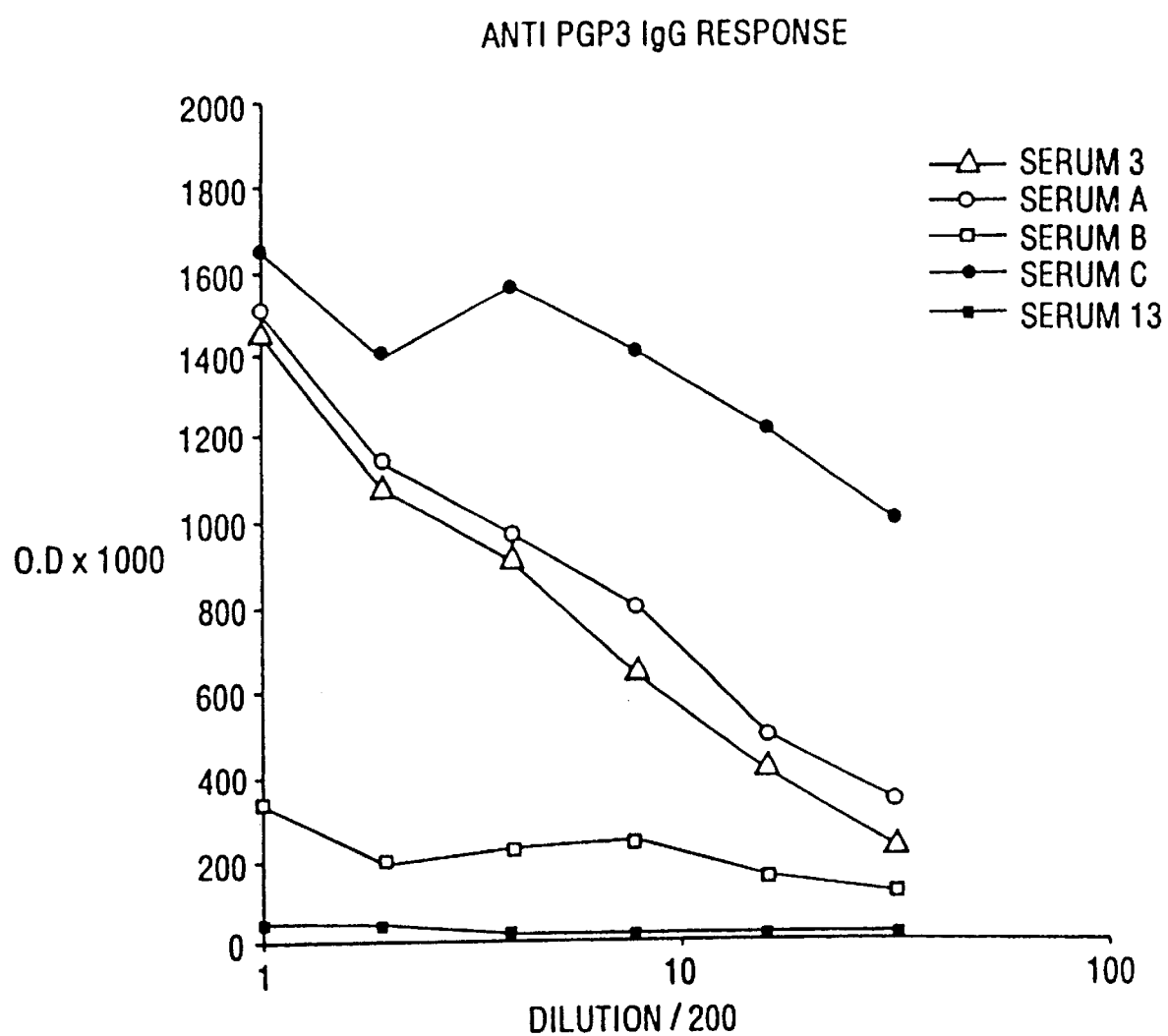
FIG. 1 demonstrates reaction of human sera with plastic-bound recombinant pgp3 protein. Results obtained with sera diluted from 200 to 6800 folds are shown. ODs are average values obtained from duplicate samples. *C. trachomatis* MIF titres of the sera (top to bottom) were 1:256, 1:128, 1:128, 1:32, zero. Sera C, A, and 3 were from women with salpingitis; the serum B was from a male with isolation-positive chlamydia urethritis; serum 13 was from a healthy blood donor.

The ORF3 sequence of pCT cloned from a serotype D isolate of *C. trachomatis* (Comanducci et al. 1990) was sub-cloned in *E. coli* strain BL21, using the plasmid expression vector pT7-7 (Tabor and Richardson, 1985). In this system the expression of ORF3 is under the control of an IPTG-inducible promoter and yields the unmodified pgp3 amino acid sequence. The recombinant pgp3 protein was purified from *E. coli* extracts by ion-change column chromatography on mono-Q prepacked columns (Pharmacia), using a NaCl elution gradient in piperazine-HCl buffer (Comanducci et al., manuscript in preparation). The final product was >90% pure pgp3 antigen, according to electrophoretic and immunoblot analyses which were done using the previously described rabbit anti serum raised aganist the 39 kDa fusion protein (Comanducci it al. 1993).

Western blot analysis and Micro-immunofluorescence (MIF) were performed according standard procedures as previously described (Comanducci et al., 1993). Human sera were titrated by single-antigen MIF using sucrose gradient purified EBs of *C. trachomatis* L2-434-Bu, *C. psittaci* 6BC and A22, *C. pneumoniae* IOL-207.

Enzyme linked immunoassay.

The appropriate amount (100–500 ng per well) of purified pgp3 antigen was diluted in 100 ul of coating buffer (PBS pH 8.0, 0.05% Tween 20, 0.02% NaN3) and adsorbed onto plastic wells of microtiter plates (NUNC), for 2 hrs at 37° C. and then overnight at 4° C. The wells then were washed several times with the PBS-Tween buffer, then saturated with 200 microliters of 2.7% Poly-vinylpirrolidone in water for 2 hr and washed again. Serum samples were serially diluted in 100 microliters of PBS, and put in contact with the plastic adsorbed antigen for 2 hrs. After adequate washings, bound serum antibodies were measured by incubating with alkaline phosphatase labelled anti-rabbit or anti-human IgG antibody (Cappel), followed by a colorimetric reaction using ELISA substrate and buffer (Sclavo) as recommended by the manufacturers. Optical density readings ere performed with a Titertek Multiscan MCC densitometer.

RESULTS AND DISCUSSION

Initial attempts of developing an ELISA test for human sera using the previously described (Comanducci et al, 1993) 39-kDa pgp3 fusion protein, purified by electrophoresis on SDS-acrylamide gels, gave inconsistent and unsatisfactory results. One of the problems was the observation that, in some patient sera, antibody reaction with minor contaminants from *E. coli* was stronger than the reaction with the denatured fusion protein. Situations like this can be adequately resolved by the Western blot technique, where signals from different antigens can be separately monitored, but they become a serious problem in ELISA. Therefore, we attempted to improve both the quality of the recombinant antigen and purification procedures. Considering that patients reacting against pgp3 during a chlamydial infection will also make antibodies against conformational epitopes (which are not expected to give an effective interaction with the largely denatured antigens usually present on Western blots), we decided to seek expression in *E. coli* of the pgp3 antigen with its native amino acid sequence and adopt a purification procedure which avoided, as much as possible, denaturing steps. This was obtained by using the pT7.7 expression system in *E. coli* BL21 cells, and column chromatography of cell extracts on a Mono-Q support. The new recombinant pgp3 antigen was initially tested ore its ability to bind to microtiter plate wells in a variety of conditions and the simple incubation in phosphate buffer and 0.05% Tween was found to be satisfactory.

Description of FIG. 1:

FIG. 1. Reaction of human sera with plastic-bound recombinant pgp3 protein. Results obtained with sera diluted from 200 to 6800 folds are shown. ODs are average values obtained form duplicate sample. C. trachomatis, MIF titres of the sera (top to bottom) were 1:256; 1:128; 1;128; 1:32; zero. Sera C, A, and 3 were from women with salpingitis; the serum B was from a male with isolation-positive chlamydial urethritia; serum 13 was from a healthy blood donor.

Rabbit sera raised against the pgp3 polypeptide (either against the 39-kDa fusion protein or the 28-kDa recombinant pgp3), and specifically recognizing a 28-kDa band in Western blots of total EB protein, were initially used for setting up the assay. Several amounts (500 ng down to 50 ng) of purified antigen in each well were tested against reference sera nd the amount of 200 ng/well was eventually chosen as a standard assay condition. A panel of 21 human sera was used to test the ELISA performance with clinical samples. All sera gave negative MIF response to C. psittaci and C. pneumoniae. When tested for C. trachomatis antibodies, using purified L2-serotype EBs, 15 sera were scored as MIF negative, and 6 positive, with titers comprised between 1:32 and 1:256. These sera were also tested for their ability to react with the purified pgp3 preparation on Western blots; all the MIF negative sera gave negative results, whereas the MIF positive sera reacted, to various extents, with the 28-kDa band only.

Two-fold serial dilutions of the sera were tested, in duplicate samples, with the pgp3-ELISA. OD readings were taken after 30 min, 1 hr and after O/N storage in the cold ($-20°$ C.). All 15 negative sera gave consistently low OD reading (below 0.1), whereas the 6 positive sera gave distinctly higher OD readings which proportionally decreased with the serum concentration in the sample. The [OD vs dilution] curves of the positive sera so far tested correlated with the MIF titres. Typical ELISA results are shown in FIG. 1.

Further work on larger numbers of clinical samples is in progress, however the results here presented indicate that this assay can be used for sensitive and quantitative detection of anti pgp3 antibodies in patient sera, and therefore will be an essential tool for studies on the significance of the immune response against this newly described antigen in the course of C. trachomatis infections.

REFERENCES

Comanducci M, Ricci S, Cevenini R, and Ratti G (1990) Plasmid 23, 149–154.

Comanducci M, Cevenini R, Ricci S, Moroni A, Scarlato V, and Ratti G (1993) J. Gen. Microbiol. 139, 1083–1092

Tabor, S. and Richardson CC (1985) Proc. Nat. Acad. Sci. USA. 262, 1074–1078

Definitions

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hanes & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR IAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

Standard abbreviations for nucleotides and amino acids are used in this specification. All publications, patents, and patent applications cited herein are incorporated by reference.

Examples of the protein that can be used in the present invention include polypeptides with minor amino acid variations from the natural amino acid sequence of the protein; in particular, conservative amino acid replacements are contemplated. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an aspartate with a glutamate, a threonine with a serine, or a similar conservative replacement of an amino acid with a structurally related amino acid will not have a major effect on the biological activity. Polypeptide molecules having substantially the same amino acid sequence as the protein but possessing minor amino acid substitutions that do not substantially affect the functional aspects are within the definition of the protein.

A significant advantage of producing the protein by recombinant DNA techniques rather than by isolating and purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants can readily be produced because the only human protein produced by the recombinant non-human host is the recombinant protein at issue. Potential viral agents from natural sources and viral components pathogenic to humans are also avoided.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mPNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki, et al., Nature 324:163 (1986); and Scharf et al., Science (1986) 233:1076–1078; and U.S. Pat. No. 4,683,195; and U.S. Pat. No. 4,683,202. As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

The protein may be used for producing antibodies, either monoclonal or polyclonal, specific to the protein. The methods for producing these antibodies are known in the art.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "genomic" is meant a collection or library of DNA molecules which are derived from restriction fragments that have been cloned in vectors. This may include all or part of the genetic material of an organism.

By "cDNA" is meant a complimentary mRNA sequence that hybridizes to a complimentary strand of mRNA.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

Expression Systems

Once the appropriate coding sequence is isolated, it can be expressed in a variety of different expression systems; for example those used with mammalian cells, baculoviruses, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual*, 2nd ed.].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci,* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual*].

Some genes may be expressed more efficiently when introns (also called intervening sequences) are present. Several cDNAs, however, have been efficiently expressed from vectors that lack splicing signals (also called splice donor and acceptor sites) [see e.g., Gothing and Sambrook (1981) *Nature* 293:620]. Introns are intervening noncoding sequences within a coding sequence that contain splice donor and acceptor sites. They are removed by a process called "splicing," following polyadenylation of the primary transcript [Nevins (1983) *Annu. Rev. Biochem.* 52:441; Green (1986) *Annu. Rev. Genet.* 20:671; Padgett et al. (1986) *Annu. Rev. Biochem.* 55:1119; Krainer and Maniatis (1988) "RNA splicing." In *Transcription and splicing* (ed. B. D. Hames and D. M. Glover)].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a procaryotic host for cloning and amplification. Examples of such mammalian-bacteria shuttle vectors include pMT2 [Kaufman et al. (1989) *Mol. Cell. Biol.* 9:946 and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988)*Ann. Rev. Microbiol.,* 42:177) and a procaryotic ampicillin-resistance (amp) gene and origin of replication for selection and propagation in *E. coli.*

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2–5 kb section of the baculovirus genome. Methods for introducing heterologous DNA into the desired site in the baculovirus virus are known in the art. (See Summers and Smith supra; Ju et al. (1987); Smith et al., Mol. Cell. Biol. (1983) 3:2156; and Luckow and Summers (1989)). For example, the insertion can be into a gene such as the polyhedrin gene, by homologous double crossover recombination; insertion can also be is into a restriction enzyme site engineered into the desired baculovirus gene. Miller et al., (1989), Bioessays 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: Aedes aegypti, Autographa californica, Bombyx mori, Drosophila melanogaster, Spodoptera frugiperda, and Trichoplusia ni (PCT Pub. No. WO 89/046699; Carbonell et al., (1985) J. Virol. 56:153; Wright (1986) Nature 321:718; Smith et al., (1983) Mol. Cell. Biol. 3:2156; and see generally, Fraser, et al. (1989) In Vitro Cell. Dev. Biol, 25:225).

Cells and cell culture media are commercially available for both direct and fusion expression of heterologous polypeptides in a baculovirus/expression system; cell culture technology is generally known to those skilled in the art. See, e.g., Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3") transcription of a coding sequence (e.g. structural gene) into mRNA. A promoter will have a transcription initiation region which isusually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in Escherichia coli (E. coli) [Raibaud et al. (1984) Annu. Rev. Genet. 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) Nature 198:1056], and maltose. Additional examples include promoter sequences derived from biosynthetic enzymes such as tryptophan (trp) [Goeddel et al. (1980) Nuc, Acids Res. 8:4057; Yelverton et al. (1981) Nucl. Acids Res. 9:731; U.S. Pat. No. 4,738,921; EPO Publ. Nos. 036 776 and 121 775]. The g-laotamase (bla) promoter system [Weissmann (1981) "The cloning of interferon and other mistakes." In Interferon 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of nonbacterial origin can also be coupled with a compatible RNA polymerase to produce high levels of expression of some genes in prokaryotes. The bacteriophage T7 RNA polymerase/promoter system is an example of a coupled promoter system (Studier et al. (1986) *J. Mol. Biol.* 189:113; Tabor et al. (1985) *Proc Natl. Acad. Sci.* 82:1074). In addition, a hybrid promoter can also be comprised of a bacteriophage promoter and an coli operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon [Shine e al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EPO Publ. No. 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic spece, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various Bacillus strains can be used to secrete heterologous proteins from *B. subtilis* [Palva et al. (1982) *Proc. Natl. Acad. Sci. USA* 79:5582; EPO Publ. No. 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicoin may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bactedrial chromosome. For example, integrating vectors constructed with DNA from various Bacillus strains integrate into the Bacillus chromosome (EPO Publ. No. 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) Annu. Rev.Microbiol. 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci, USA* 79:5582; EPO Publ. Nos. 036 259 and 063 953; PCT Publ. No. WO 84/04541], *Escherichia coli* [Shimatake et al. (1981) *Nature* 292:128; Amann et al. (1985) *Gene* 40:183; Studier et al. (1986) *J. Mol. Biol.* 189:113; EPO Publ. Nos. 036 776, 136 829 and 136 907], *Streptococcus cremoris* [Powell et al. (1988) Appl. Environ. Microbiol. 54:655]; *Streptococcus lividans* [Powell et al. (1988) *Appl, Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al. (1989) *FEMS Microbiol. Lett.* 60:273; Palva et al. (1982) *Proc. Natl. Acad. Sci. USA* 79:5582; EPO Publ. Nos. 036 259 and 063 953; PCT Publ. No. WO 84/04541, Bacillus], [Miller et al. (1988) *Proc. Natl. Acad. Sci.* 85:856; Wang et al. (1990) *J. Bacteriol.* 172:949, Campylobacter], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; Escherichia], [Chassy et al. (1987) *FEMS Microbiol. Lett.* 44:173 Lactobacillus]; [Fiedler et al. (1988) *Anal. Biochem* 170:38, Pseudomonas]; [Augustin et al. (1990) *FEMS Microbiol. Lett.* 66:203, Staphylococcus], [Barany et al. (1980) *J. Bacteriol.* 144:698; Harlander (1987) "Transformation oStreptococcus lactis by electroporation, in: *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, Streptococcus].

iv. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes i the Yeast Saccharomyces cerevisiae," in: *Plasmids of Medical. Environmental and Commercial Importance* (eds. K>N>Timmis and A. Puhler); Mercerau-Puigalon et al. (1980) *Gene* 11:163; Panthier et al. (1980) *Curr. Genet,* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Publ. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (see, e.g., PCT Publ. No. WO 88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588, 684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EPO Publ. No. 324 274). Additional leaders employing an alpha-factor leader fragment that provides for secretion include hybrid alpha-factor leaders made with a presequence of a first yeast, but a pro-region from a second yeast alphafactor. (See e.g., PCT Publ. No. WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 [Botstein et al. (1979) *Gene* 8:17–24], pCl/1 [Brake et al. (1984) *Proc. Natl. Acad. Sci USA* 81:4642–4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228–245]. An integrating vector may be directed to a specific locus in yeast by selecting the appropriate homologous sequence for inclusion in the vector. See Orr-Weaver et al. supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol. Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts:*Candida albicans* [Kurtz, et al. (1986) *Mol. Cell. Biol,* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkar et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNR into yeast hosts are well-known in the art, and usually include either the transformation of spheroplasts or of intact yeast cells treated with alkali cations. Transformation procedures usually vary with the yeast species to be transformed. See e.g., [Kurtz et al. (1986) *Mol. Cell, Biol.* 6:142; Kunze et al. (1985) *J. Basic Microbiol,* 25:141; Candida]; [Gleeson et al. (1986) *J. Gen. Microbiol.* 132:3459; Roggenkamp et al. (1986) *Mol. Gen. Genet.* 202:302; Hansenula]; [Das et al. (1984) *J. Bacteriol.* 158:1165; De Louvencourt et al. (1983) *J. Bacteriol.* 154:1165; Van den Berg et al. (1990) *Bio/Technology* 8:135; Kluyveromyces]; [Cregg et al. (1985) *Mol. Cell. Biol,* 5:3376; Kunze et al. (1985) *J. Basic Microbiol.* 25:141; U.S. Pat. Nos. 4,837,148 and 4,929,555; Pichia]; [Hinnen et al. (1978) *Proc. Natl. Acad. Sci. USA* 75;1929; Ito et al. (1983) *J. Bacteriol.* 153:163 Saccharomyces]; [Beach and Nurse (1981) *Nature* 300:706; Schizosaccharomyces]; [Davidow et al. (1985) *Curr. Genet.* 10:39; Gaillardin et al. (1985) *Curr. Genet.* 10:49; Yarrowia].

Nucleic Acid Assays

Polynucleotide probes of approximately 8 nucleotides or more can be prepared which hybridize with the positive strand(s) of the RNA or its complement, as well as to cDNAs. These polynucleotides serve as probes for the detection, isolation and/or labeling of polynucleotides which contain nucleotide sequences, and/or as primers for the transcription and/or replication of the targeted sequences. Each probe contains a targeting polynucleotide sequence, which is comprised of nucleotides which are complementary to a target nucleotide sequence; the sequence is of sufficient length and complementarily with the sequence to form a duplex which has sufficient stability for the purpose intended. For example, if the purpose is the isolation, via immobilization, of an analyte containing a target sequence, the probes will contain a polynucleotide region which is of sufficient length and complementarily to the targeted sequence to afford sufficient duplex stability to immobilize the analyte on a solid surface under the isolation conditions. For example, also, if the polynucleotide probes are to serve as primers for the transcription and/or replication of target sequences, the probes will contain a polynucleotide region of sufficient length and complementarily to the targeted sequence to allow for replication. For example, also, if the polynucleotide probes are to be used as label probes, or are to bind to multimers, the targeting polynucleotide region would be of sufficient length and complementarily to form stable hybrid duplex structures with the label probes and/or multimers to allow detection of the duplex. The probes may contain a minimum of about 4 contiguous nucleotides which are complementary to the targeted sequence; usually the oligomers will contain a minimum of about 8 is continuous nucleotides which are complementary to the targeted sequence, and preferably will contain a minimum of about 14 contiguous nucleotides which are complementary to the targeted sequence.

The probes, however, need not consist only of the sequence which is complementary to the targeted sequence. They may contain additional nucleotide sequences or other moieties. For example, if the probes are to be used as primers for the amplification of sequences via PCR, they may contain sequences which, when in duplex, form restriction enzyme sites which facilitate the cloning of the amplified sequences. For example, also, if the probes are to be used as "capture probes" in hybridization assays, they will be coupled to a "binding partner" as defined above. Preparation of the probes is by means known in the art, including, for example, by methods which include excision, transcription or chemical synthesis.

Immunodiagnostic Assays

Antigens can be used in immunoassays to detect antibody levels (or conversely antibodies can be used to detect antigen levels) and correlation can be made with disease. Immunoassays based on well defined, recombinant antigens can be developed to replace the invasive diagnostics methods that are used today. Antibodies to proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Vaccines

Vaccines may either be prophylactic (to prevent infection) or therapeutic (to treat disease after infection).

Such vaccines comprise antigen or antigens, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc; and (6) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individuals immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

EXAMPLES

The examples presented herein are provided as a further is guide to the practitioner of ordinary skill in the art and are not to be construed as limiting the invention in any way.

What is claimed is:

1. A recombinant polynucleotide encoding a recombinant *Chlamydia trachomatis* non-fusion pgp3 protein comprising the sequence of SEQ ID NO: 2.

2. A vector comprising a recombinant polynucleotide according to claim 1.

3. A host cell transformed with a vector according to claim 2.

4. A method for preparing a recombinant non-fusion pgp3 protein of *Chlamydia trachomatis* comprising transforming a host cell with the vector of claim 2.

* * * * *

UNITED STATES PATENT AND TRADEMARK OFFICE
CERTIFICATE OF CORRECTION

PATENT NO.   : 6,210,968 B1
DATED        : April 3, 2001
INVENTOR(S)  : Ratti

It is certified that error appears in the above-identified patent and that said Letters Patent is hereby corrected as shown below:

<u>Title page,</u>
Item [56], OTHER PUBLICATIONS, please delete the second occurrence of "Comanducci M. et al." publication;

<u>Column 1,</u>
Line 9, CROSS REFERENCE TO RELATED APPLICATIONS, please delete "pending" and insert therefor -- now U.S. Patent No. 5,629,167, issued on May 13, 1997, incorporated herein by reference in its entirety --;

<u>Column 2,</u>
Line 17, please delete "(Comanducci it al. 1993)." and insert therefor -- (Comanducci et al. 1993). --.
Line 66, please delete "ore" and insert therefor -- for --;

<u>Column 3,</u>
Line 7, please delete "sample" and insert therefor -- samples --;
Line 18, please delete "nd" and insert therefor -- and --;

<u>Column 4,</u>
Line 5, please delete "IAN" and insert therefor -- Mammalian --;

<u>Column 5,</u>
Line 51, please "MPNA" and insert therefor -- mRNA --;

<u>Column 11,</u>
Line 17, please delete "2-5kb" and insert therefor -- 25kb --;

UNITED STATES PATENT AND TRADEMARK OFFICE
CERTIFICATE OF CORRECTION

PATENT NO.    : 6,210,986 B1
DATED         : April 3, 2001
INVENTOR(S)   : Ratti It is certified that error appears in the above-identified patent and that said Letters Patent is hereby corrected as shown below:

Column 13,
Line 25, please delete "coli" and insert therefor -- E Coli --;

Signed and Sealed this

Twenty-first Day of January, 2003

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 792 base pairs
        (B) TYPE: nucleic acid
        (C) STRANDEDNESS: single
        (D) TOPOLOGY: linear (xi) SEQUENCE DESCRIPTION: SEQ ID NO:1:

```
ATG GGA AAT TCT GGT TTT TAT TTG TAT AAC ACT GAA AAC TGC GTC           45
Met Gly Asn Ser Gly Phe Tyr Leu Tyr Asn Thr Glu Asn Cys Val
1               5                   10                  15

TTT GCT GAT AAT ATC AAA GTT GGG CAA ATG ACA GAG CCG CTC AAG           90
Phe Ala Asp Asn Ile Lys Val Gly Gln Met Thr Glu Pro Leu Lys
                20                  25                  30

GAC CAG CAA ATA ATC CTT GGG ACA ACA TCA ACA CCT GTC GCA GCC          135
Asp Gln Gln Ile Ile Leu Gly Thr Thr Ser Thr Pro Val Ala Ala
                35                  40                  45

AAA ATG ACA GCT TCT GAT GGA ATA TCT TTA ACA GTC TCC AAT AAT          180
Lys Met Thr Ala Ser Asp Gly Ile Ser Leu Thr Val Ser Asn Asn
                50                  55                  60

TCA TCA ACC AAT GCT TCT ATT ACA ATT GGT TTG GAT GCG GAA AAA          225
Ser Ser Thr Asn Ala Ser Ile Thr Ile Gly Leu Asp Ala Glu Lys
                65                  70                  75

GCT TAC CAG CTT ATT CTA GAA AAG TTG GGA GAT CAA ATT CTT GAT          270
Ala Tyr Gln Leu Ile Leu Glu Lys Leu Gly Asp Gln Ile Leu Asp
                80                  85                  90

GGA ATT GCT GAT ACT ATT GTT GAT AGT ACA GTC CAA GAT ATT TTA          315
```

```
Gly Ile Ala Asp Thr Ile Val Asp Ser Thr Val Gln Asp Ile Leu
                95                 100                 105

GAC AAA ATC AAA ACA GAC CCT TCT CTA GGT TTG TTG AAA GCT TTT                360
Asp Lys Ile Lys Thr Asp Pro Ser Leu Gly Leu Leu Lys Ala Phe
                110                 115                 120

AAC AAC TTT CCA ATC ACT AAT AAA ATT CAA TGC AAC GGG TTA TTC                405
Asn Asn Phe Pro Ile Thr Asn Lys Ile Gln Cys Asn Gly Leu Phe
                125                 130                 135

ACT CCC AGT AAC ATT GAA ACT TTA TTA GGA GGA ACT GAA ATA GGA                450
Thr Pro Ser Asn Ile Glu Thr Leu Leu Gly Gly Thr Glu Ile Gly
                140                 145                 150

AAA TTC ACA GTC ACA CCC AAA AGC TCT GGG AGC ATG TTC TTA GTC                495
Lys Phe Thr Val Thr Pro Lys Ser Ser Gly Ser Met Phe Leu Val
                155                 160                 165

TCA GCA GAT ATT ATT GCA TCA AGA ATG GAA GGC GGT GTT GTT CTA                540
Ser Ala Asp Ile Ile Ala Ser Arg Met Glu Gly Gly Val Val Leu
                170                 175                 180

GCT TTG GTA CGA GAA GGT GAT TCT AAG CCC TGC GCG ATT AGT TAT                585
Ala Leu Val Arg Glu Gly Asp Ser Lys Pro Cys Ala Ile Ser Tyr
                185                 190                 195

GGA TAC TCA TCA GGC ATT CCT AAT TTA TGT AGT CTA AGA ACC AGT                630
Gly Tyr Ser Ser Gly Ile Pro Asn Leu Cys Ser Leu Arg Thr Ser
                200                 205                 210

ATT ACT AAT ACA GGA TTG ACT CCG ACA ACG TAT TCA TTA CGT GTA                675
Ile Thr Asn Thr Gly Leu Thr Pro Thr Thr Tyr Ser Leu Arg Val
                215                 220                 225

GGC GGT TTA GAA AGC GGT GTG GTA TGG GTT AAT GCC CTT TCT AAT                720
Gly Gly Leu Glu Ser Gly Val Val Trp Val Asn Ala Leu Ser Asn
                230                 235                 240

GGC AAT GAT ATT TTA GGA ATA ACA AAT ACT TCT AAT GTA TCT TTT                765
Gly Asn Asp Ile Leu Gly Ile Thr Asn Thr Ser Asn Val Ser Phe
                245                 250                 255

TTA GAG GTA ATA CCT CAA ACA AAC GCT                                        792
Leu Glu Val Ile Pro Gln Thr Asn Ala
                260

(2) INFORMATION FOR SEQ ID NO:2:

(i) SEQUENCE CHARACTERISTICS:
        (A) LENGTH: 264 amino acids
        (B) TYPE: amino acid
        (C) STRANDEDNESS: single
        (D) TOPOLOGY: linear (xi) SEQUENCE DESCRIPTION: SEQ ID NO:2:

Met Gly Asn Ser Gly Phe Tyr Leu Tyr Asn Thr Glu Asn Cys Val
1               5                   10                  15

Phe Ala Asp Asn Ile Lys Val Gly Gln Met Thr Glu Pro Leu Lys
                20                  25                  30

Asp Gln Gln Ile Ile Leu Gly Thr Thr Ser Thr Pro Val Ala Ala
                35                  40                  45

Lys Met Thr Ala Ser Asp Gly Ile Ser Leu Thr Val Ser Asn Asn
                50                  55                  60

Ser Ser Thr Asn Ala Ser Ile Thr Ile Gly Leu Asp Ala Glu Lys
                65                  70                  75

Ala Tyr Gln Leu Ile Leu Glu Lys Leu Gly Asp Gln Ile Leu Asp
                80                  85                  90

Gly Ile Ala Asp Thr Ile Val Asp Ser Thr Val Gln Asp Ile Leu
                95                  100                 105
```

-continued

```
Asp Lys Ile Lys Thr Asp Pro Ser Leu Gly Leu Leu Lys Ala Phe
            110                 115                 120

Asn Asn Phe Pro Ile Thr Asn Lys Ile Gln Cys Asn Gly Leu Phe
            125                 130                 135

Thr Pro Ser Asn Ile Glu Thr Leu Leu Gly Gly Thr Glu Ile Gly
            140                 145                 150

Lys Phe Thr Val Thr Pro Lys Ser Ser Gly Ser Met Phe Leu Val
            155                 160                 165

Ser Ala Asp Ile Ile Ala Ser Arg Met Glu Gly Gly Val Val Leu
            170                 175                 180

Ala Leu Val Arg Glu Gly Asp Ser Lys Pro Cys Ala Ile Ser Tyr
            185                 190                 195

Gly Tyr Ser Ser Gly Ile Pro Asn Leu Cys Ser Leu Arg Thr Ser
            200                 205                 210

Ile Thr Asn Thr Gly Leu Thr Pro Thr Thr Tyr Ser Leu Arg Val
            215                 220                 225

Gly Gly Leu Glu Ser Gly Val Val Trp Val Asn Ala Leu Ser Asn
            230                 235                 240

Gly Asn Asp Ile Leu Gly Ile Thr Asn Thr Ser Asn Val Ser Phe
            245                 250                 255

Leu Glu Val Ile Pro Gln Thr Asn Ala
            260
```

(2) INFORMATION FOR SEQ ID NO:3:

(i) SEQUENCE CHARACTERISTICS:
        (A) LENGTH: 28 bases
        (B) TYPE: nucleic acid
        (C) STRANDEDNESS: single
        (D) TOPOLOGY: linear (xi) SEQUENCE DESCRIPTION: SEQ ID NO:3:

CAGGGATCCA TGGGAAATTC TGGTTTTT                    28

(2) INFORMATION FOR SEQ ID NO:4:

(i) SEQUENCE CHARACTERISTICS:
        (A) LENGTH: 28 bases
        (B) TYPE: nucleic acid
        (C) STRANDEDNESS: single
        (D) TOPOLOGY: linear (xi) SEQUENCE DESCRIPTION: SEQ ID NO:4:

CCCCTGCAGT TAAGCGTTTG TTTGAGGT                    28